United States Patent [19]
Blanchard et al.

[11] Patent Number: 4,906,649
[45] Date of Patent: Mar. 6, 1990

[54] USE OF A COMPOUND FOR THE TREATMENT OF SLEEP DISORDERS AND DEPRESSION

[75] Inventors: Jean-Charles Blanchard, Saint Mandé; Pierre Laduron, Paris; Jean-Maris Stutzmann, Villecresnes, all of France

[73] Assignee: Rhone-Poulenc Sante, Antony, France

[21] Appl. No.: 234,600

[22] Filed: Aug. 22, 1988

[30] Foreign Application Priority Data

Aug. 25, 1987 [FR] France ................................ 87 11884

[51] Int. Cl.$^4$ ........................................... A61U 31/425
[52] U.S. Cl. .................................................. 514/367
[58] Field of Search ......................................... 514/367

[56] References Cited

FOREIGN PATENT DOCUMENTS 0050551  4/1982  European Pat. Off. .

OTHER PUBLICATIONS

Chem. Abst., 97(1982)-44352y.
Chem. Abst., 109(1988)-31973t.
Stedman's Medical Dictionary, 23rd Ed., (1976), p. 676.

Primary Examiner—Stanley J. Friedman
Attorney, Agent, or Firm—Stevens, Davis, Miller & Mosher

[57] ABSTRACT 2-amino-6-(trifluoromethoxy)benzothiazole may be used in the production of a sleep-regulating medicinal product, which is useful in the treatment of sleep disorders and in the treatment of depression.

2 Claims, No Drawings

USE OF A COMPOUND FOR THE TREATMENT OF SLEEP DISORDERS AND DEPRESSION

The present invention relates to the application of 2-amino-6-(trifluoromethoxy)benzothiazole or a pharmaceutically acceptable salt thereof for obtaining a sleep-regulating medicinal product which is useful in the treatment of sleep disorders and in the treatment of depression.

It is known from European Patent 50,551 that 2-amino-6-(trifluoromethoxy)benzothiazole is useful as an anticonvulsant, anxiolytic and hypnotic medicinal product.

It has now been found that 2-amino-6-(trifluoromethoxy)benzothiazole or a pharmaceutically acceptable salt thereof has an action on slow-wave sleep and also on paradoxical sleep. It is hence useful in the treatment of sleep disorders and the treatment of depression, a disease in which it is known that the amount of paradoxical sleep and the latency of onset of the paradoxical sleep phases are reduced (MENDLEWICZ et al., Acta Psychiat. Scand. 320, 26–29, 1985).

The properties with respect to sleep were determined in rats according to the following protocol:

in male rats (CD, C.O.B.S., Ch. RIVER, FRANCE), weighing from 300 to 400 g, cortical electrodes (somataesthetic and visual areas) and muscular electrodes (muscle of the nape of the neck) are permanently implanted. One week later, polygraph recording can begin. From an electroencephalographic (EEG) standpoint, 4 stages, corresponding to different levels of vigilance, are defined in rats:

wakefulnesss
drowsiness
slow-wave sleep
paradoxical sleep.

For each rat, the EEG traces are collected during 7 hours on the day before administration (day $D_1$) and the day of administration (day $D_2$) of the product. The percentage distribution of the different stages of the waking-sleeping cycle is then calculated with respect to the total recording time. For each dose of product, the means percentages calculated for each of the stages on day $D_1$ are then compared with the corresponding mean percentages calculated on day $D_2$.

The compound is administered orally (5 cc/kg) at doses of 0.5, 2 and 8 mg/kg, dissolved in 1 N hydrochloric acid (0.2 cc). 4 to 5 animals are used per dose.

At a dose of 0.5 mg/kg p.o., the compound does not modify the distribution of the waking-sleeping cycle. In contrast, at doses of 2 and 8 mg/kg p.o., this compound significantly reduces wakefulness ($-27\%$, $p<0.01$, and $-39\%$, $p<0.01$, respectively) in favour of slow-wave sleep ($+46\%$, $p<0.05$, and $+57\%$, $p<0.05$, respectively) and paradoxial sleep ($+84\%$, $p<0.01$, and $+79\%$, $p<0.05$, respectively).

Overall, the compound hence increases slow-wave sleep and paradoxical sleep at the expense of wakefulness at doses of 2 mg/kg p.o. and above in rats.

2-Amino-6-(trifluoromethoxy)benzothiazole has low toxicity. Its oral $LD_{50}$ in mice is 67 mg/kg. This $LD_{50}$ was calculated after 3 days of observation by the cumulative method of J.J. REED and H. MUENCH, Amer. J. HYG 1938, 27, 493.

2-Amino-6-(trifluoromethoxy)benzothiazole may be prepared according to the process described in Patent EP 50,551.

The sleep-regulating medicinal products consist of 2-amino-6-(trifluoromethoxy)benzothiazole or pharmaceutically acceptable salt thereof either alone or in the form of a composition in which it is combined with any other pharmaceutically compatible product, which may be inert or physiologically active. These medicinal products may be used orally, parenterally or rectally.

As solid compositions for oral administration, tablets, pills, powders (gelatin capsules, wafer tablets) or granules may be used. In these compositions, the active principle is mixed with one or more inert diluents such as starch, cellulose, sucrose, lactose or silica. These compositions can also comprise substances other than diluents, e.g. one or more lubricants such as magnesium stearate or talc, a colouring, a coating (dragees) or a lacquer.

As liquid compositions for oral administration, there may be used solutions, suspensions, emulsions, syrups and elixirs which are pharmaceutically acceptable, containing inert diluents such as water, ethanol, glycerol, vegetable oils or liquid paraffin. These compositions can comprise substances other than diluents, e.g. wetting, sweetening, thickening, flavouring or stabilizing products.

The compositions for parenteral administration may be sterile suspensions, emulsions or nonaqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization can be carried out in several ways, e.g. by aseptic filtration, by incorporating sterilizing agents in the composition, by irradiation or by heating. They can also be prepared in the form of sterile solid compositions which can be dissolved in an injectable sterile medium immediately prior to administration.

The compositions for rectal administration may be suppositories or rectal capsules containing, apart from the active product, excipients such as cocoa butter, semi-synthetic glycerides or polyethylene glycol.

In human therapy, 2-amino-6-(trifluoromethoxy)benzothiazole or pharmaceutically acceptable salt thereof is useful as a sleep regulator, in particular in the treatment of sleep disorders and in the treatment of depression.

The doses depend on the effect desired, on the length of the treatment and on the administration route used; they are generally between 10 and 100 mg orally per day for an adult, with unit doses ranging from 2 to 50 mg of active substance.

Generally speaking, the doctor will determine the appropriate dosage in accordance with the age, weight and all other factors specific to the subject to be treated.

The examples which follow illustrate pharmaceutical compositions which are useable as a sleep regulator.

EXAMPLE A

Gelatin capsules containing a 25-mg dose of active product and having the following composition are prepared according to the usual technique:

| | |
|---|---|
| 2-amino-6-(trifluoromethoxy)benzothiazole | 25 mg |
| microcrystalline cellulose | 75 mg |
| mannitol | 41 mg |
| colloidal silica | 4 mg |
| sodium carboxymethylstarch | 25 mg |
| talc | 18 mg |

-continued

| | |
|---|---|
| magnesium stearate | 2 mg |
| polyvidone excipient | 10 mg |

EXAMPLE 8

Tablets containing a 50-mg dose of active product and having the following composition are prepared according to the usual technique:

| | |
|---|---|
| 2-amino-6-(trifluoromethoxy)benzothiazole | 50 mg |
| monocrystalline cellulose | 75 mg |
| mannitol | 41 mg |
| polyvidone excipient | 10 mg |
| carboxymethylstarch | 25 mg |
| colloidal silica | 4 mg |
| talc | 18 mg |
| magnesium stearate | 2 mg |
| mixture of hydroxymethylcellulose, glycerin and titanium oxide (72:3.5:24.5) | 245 mg |
| qs 1 complete finished film-coated tablet weighing | |

EXAMPLE C

An injectable solution is prepared, containing 10 mg of active product and having the following composition:

| | |
|---|---|
| 2-amino-6-(trifluoromethoxy)benzothiazole | 10 mg |
| benzoic acid | 80 mg |
| benzyl alcohol | 0.06 cc |
| sodium benzoate | 80 mg |
| ethanol, 95% strength | 0.4 cc |
| sodium hydroxide | 24 mg |
| propylene glycol | 16 cc |
| water | qs 4 cc |

We claim:

1. Method of treatment of depression comprising administering to a subject suffering therefrom or liable thereto an effective amount of 2-amino-6-(trifluoromethoxy)benzothiazole or a pharmaceutically acceptable salt thereof to treat depression.

2. A method of treating a condition due to lack of paradoxical sleep comprising administering to a patient suffering therefrom or liable thereto 2-amino-6-trifluoromethoxy)-benzothiazole or a pharmaceutically acceptable salt thereof in an amount sufficient to increase paradoxical sleep.

* * * * *